United States Patent [19]

White et al.

[11] Patent Number: 5,032,521

[45] Date of Patent: Jul. 16, 1991

[54] MONOCLONAL ANTIBODY SPECIFIC FOR A MAMMARY TUMOR CELL SURFACE ANTIGEN

[75] Inventors: Christine A. White, Encinitas; Renato Dulbecco, La Jolla; William R. Allen, Encinitas, all of Calif.

[73] Assignee: The Salk Institute for Biological Studies, San Diego, Calif.

[21] Appl. No.: 29,373

[22] Filed: Mar. 23, 1987

Related U.S. Application Data

[63] Continuation-in-part of Ser. No. 678,261, Dec. 5, 1984, abandoned.

[51] Int. Cl.$^5$ .................... C12N 5/20; C12N 15/06; C12P 21/08; C07K 15/28

[52] U.S. Cl. .................... 435/240.27; 435/70.2; 435/70.21; 435/172.2; 435/240.26; 530/387; 530/808; 530/809; 935/89; 935/95; 935/104; 935/107; 935/108; 935/110

[58] Field of Search .................... 435/68, 172.2, 240.27, 435/948, 70.2, 70.21, 240.26; 436/548; 935/104, 107, 110, 89, 95, 108; 530/387, 808, 809

[56] References Cited

U.S. PATENT DOCUMENTS

| | | | |
|---|---|---|---|
| 4,172,124 | 10/1979 | Koprowski et al. | 435/68 |
| 4,522,918 | 6/1985 | Schlom et al. | 435/948 |
| 4,707,438 | 11/1987 | Keydar | 435/5 |
| 4,753,894 | 6/1988 | Frankel et al. | 436/548 |

FOREIGN PATENT DOCUMENTS

| | | | |
|---|---|---|---|
| 0118365 | 4/1984 | European Pat. Off. | 435/68 |
| 0220858 | 5/1987 | European Pat. Off. | 435/172.2 |
| 02424154 | 10/1987 | European Pat. Off. | 435/68 |

OTHER PUBLICATIONS

R. Dulbecco et al., *Proc. Natl. Acad. Sci. U.S.A. 80* pp. 1033–1037 (1983).

R. Allen et al., *Proc. Natl. Acad. Sci. U.S.A. 81* pp. 1203–1027 (1984).

Ciocca et al, "Immunchistochemical Detection of an Estrogen-Regulated Protein by Monoclonal Antibodies" *Cancer Research* 42 pp. 4256–4258 (1982).

Colcher et al, "A Spectrum of Moncolonal Antibodies Reactive with Human Mammary Tumor Cells" *Proceedings of the National Academy of Sciences* 78(5) pp. 3199–203 (1981).

Taylor-Papadimitriou et al, "Moncclonal Antibodies to Epithelium-Specific Components of the Human Milk . . . " *International Journal of Cancer* 28 pp. 17–21 (1981).

Chu et al, "Monoclonal Antibodies to Human Breast Carcinoma Cells and Their Use in Diagnosis and Therapy" European patent Application EP 118,365, 12 Sep. 1984 C.A. 101: 228450m.

Stocker et al, "Generation of 2 New Mouse Myeloma Cell Lines PAI and PAI-O for Hybridoma Production" *Research Disclosure* May 1982 pp. 155–157.

Yuan et al, "Characterization of a Monoclonal Antibody Reactive with a Subset of Human Breast Tumors" *Journal of the National Cancer Institute* 68(5) pp. 719–728 (1982).

*Primary Examiner*—Elizabeth C. Weimar
*Assistant Examiner*—Gail Poulos
*Attorney, Agent, or Firm*—Fitch, Even, Tabin & Flannery

[57] ABSTRACT

Hybridomas are provided which secrete an IgG1 or IgG2 monoclonal antibody which binds to an epitope on an antigen, which occurs in the plasma membrane of MCF-7 cells and has a molecular weight of 22 kD. The epitope of the antibodies is exposed on the extracellular side of the plasma membrane of the MCF-7 cells. The monoclonal antibodies, which react generally with human mammary carcinoma cells, but with few non-mammary cancer cells, are useful diagnostically and therapeutically.

9 Claims, No Drawings

MONOCLONAL ANTIBODY SPECIFIC FOR A MAMMARY TUMOR CELL SURFACE ANTIGEN

The United States Government has certain rights in the invention disclosed herein as a consequence of support of work related to the invention under a grant from the United States National Institutes of Health.

This application is a continuation-in-part of application Ser. No. 678,261 filed Dec. 5, 1984 now abandoned.

The present invention is related to monoclonal antibodies and more particularly to monoclonal antibodies reactive with an antigen found on mammary tumor cell surfaces.

BACKGROUND OF THE INVENTION

Antibodies have long been used in medical diagnosis, e.g., determining blood types, and in biological experimentation. With development of techniques of producing monoclonal antibodies which make it possible to obtain homogenous, highly specific antibodies, Kohler G. and Milstein, C.: (1975) Nature (London) 256 495–497, the utility of antibodies has been greatly increased. Unlike antibody fractions which were previously available and which were actually heterogeneous mixtures of a number of antibody molecules reactive with a variety of antigenic determinants, the antibody molecules in a monoclonal antibody preparation all have the same idiotype and, consequently, generally are reactive with a single antigenic determinant ("epitope") or a group of structurally closely related antigenic determinants. Monoclonal antibodies are therefore much more precise probes for detecting the presence of a particular substance than were previous heterogeneous antibody fractions. The precise selectivity of monoclonal antibodies makes them particularly useful for diagnostic purposes and even as therapeutic agents against selected biological material, such as tumor cells. Monoclonal antibodies have been used to detect and isolate biological substances which were were previously unknown.

Generally, monoclonal antibodies are produced by immunizing an animal with a biological specimen or other foreign substance, obtaining antibody-producing cells from the animal, and fusing the antibody-producing cells with strains of neoplastic cells, e.g., tumor cells, to produce hybridomas which are isolated and cultured as monoclones. The monoclonal hybridomas may either be cultured in vitro or may be grown in vivo as ascites tumors in a host animal.

As understood in the art, all antibody-producing cells of an hybridoma culture derived from a single hybridoma cell produce antibodies of the same idiotype but, due to class-switching that might occur in some cells in the culture, possibly variable isotype.

As used herein, a "culture of an hybridoma" means a culture derived from a single hybridoma cell, i.e. a monoclonal hybridoma culture. "Culture," unless otherwise qualified, also means an ascites tumor, established with an aliquot of a culture of an hybridoma, and the associated ascites fluid. The "monoclonal antibodies" that are secreted by the cells of such a culture will have the same idiotype but might have different isotypes.

Not all of the hybridomas which result from fusing neoplastic cells with antibody-producing cells secrete antibody with desired idiotype, specific for the foreign substance or antigen used to immunize the animal from which the antibody-producing cells were taken, because not all of the antibody-producing cells from the immunized animal used in making the hybridomas produce antibody against that foreign substance or antigen. Indeed, the antigenic determinant of the foreign substance or antigen recognized by the monoclonal antibody from one such hybridoma culture might differ from the antigenic determinant of the same foreign substance or antigen recognized by the monoclonal antibody from another such hybridoma culture. Thus, it is necessary to screen antibody from an hybridoma culture, usually in combination with the culture medium or ascites fluid of the culture, for specificity by determining not only the ability of the antibody to recognize the foreign substance or antigen of interest but also its ability to recognize other biological materials that might occur in systems with which the antibody is to be used. While the necessity of characterizing the antibody of each clone by screening adds to the complexity of producing monoclonal antibodies, the wide variety of homogeneous antibodies which may be obtained gives investigators a number of very precise tools to map the structure and development of somatic cells.

SUMMARY OF THE INVENTION

Monoclonal antibodies, with idiotypes specific for epitopes that are exposed extracellularly on an antigen or antigens which are found predominantly on the surfaces of mammary tumor cells, are provided from cultured hybridomas. In the case of MCF-7 cells, the antibodies of the invention recognize an antigen which is a 22 kD plasma membrane protein.

Mice are inoculated with human mammary tumor cells, and spleen cells or lymph node cells are obtained from the inoculated mice and fused with mouse tumor cells. Monocultures of the fused cells are produced, and the antibodies obtained from the monoclones are tested for their ability to react with a variety of randomly obtained human mammary tumor tissues. In order to select a monoculture which produces an antibody with the desired characteristics, the reactivity of the antibody with other cells, including both normal human cells and other human tumor cells is investigated. Monoclonal antibody from one hybridoma culture, designated 15A8, is reactive with a mammary tumor cell surface antigen and is useful for diagnosing mammary tumors and, as a part of an immunotoxin (e.g., conjugated with a toxin such as gelonin), is potentially useful therapeutically as an agent against mammary tumors.

DETAILED DESCRIPTION OF THE PREFERRED EMBODIMENTS

Human mammary carcinoma currently represents the leading cause of cancer death in women in the United States with more than 150,000 new cases diagnosed each year. The histopathological classification of human mammary carcinomas is currently dependent on morphologic description alone. Approximately 80% are infiltrating ductal carcinomas, 10% are infiltrating lobular carcinomas, and the remaining 10% comprise a number of histologic types including intraductal carcinoma. Excepting inflammatory carcinoma, for the most part, morphology has not proven to be a good predictor of clinical prognosis or response to therapy. Indeed, extent of disease (tumor size and nodal positivity) have continued to determine clinical management. Recently, with the advent of estrogen and progesterone receptor determinations, correlations have begun to be made between clinical variables and biologic characteristics of malignant mammary cells.

The invention entails hybridomas and cultures thereof, antibodies made by the hybridomas and cultures of the invention, and methods of making and using the hybridomas, hybridoma cultures, and antibodies of the invention.

In accordance with the invention, hybridomas are developed which produce monoclonal antibodies which are generally reactive with human mammary carcinoma cells, specifically reacting with a cell surface antigen that is prevalent on mammary tumor cell surfaces. The antigen is MCF-7 cells recognized by the antibodies of the invention is a 22 kD plasma membrane protein that is bound by antibodies 15A8 (IgG1), 15A8 (IgG$_{2a}$) and 15A8 (IgG$_{2b}$), described further below.

The antibodies of the invention have the reactivity, with cells in culture and tissue sections, characteristic of the 15A8 antibodies. The antibody from hybridoma culture 15A8 (primarily of IgG1 isotype) reacted with 28 of 31 randomly obtained human mammary carcinomas tested, reacts more weakly with normal human epithelial cells of breast, renal proximal tubule, bladder, skin, esophagus and salivary gland, but cells of substantially no other normal tissue, and was unreactive with 14 of 18 other malignant tissues tested. Because the mammary carcinoma tissues were randomly obtained, the antibody is expected to react with about the same proportion of other randomly obtained human mammary.

As the antibodies of the invention detect an antigen found predominantly in human mammary carcinomas, they are useful in determining the cellular lineage from which human mammary carcinomas arise and have potential therapeutic utility, alone or as part of immunotoxins (i.e. conjugate of an antibody molecule with one or more molecules of a toxin, e.g. gelonin coupled through a standard linking agent such as SPDP), in breast cancer treatment.

A monoclonal antibody to the breast carcinoma cell line MCF-7 was produced utilizing the technique of Kohler and Milstein supra. The mammary tumor cell line MCF-7 (Soule, H. D., et al. *JNCI*, 51:1409–1413 (1973)) (e.g., ATCC deposit no. HTB-22), was cultured in DMEM with 10% fetal calf serum and NEAA (8.9 mg/L L-alanine, 15.0 mg/L L-asparagine, 13.3 mg/L L-aspartic acid, 14.7 mg/L L-glutamic acid, 7.5 mg/L L-glycine, 11.5 mg/L L-proline, 10.5 mg/L L-serine).

BALB/c mice were immunized with $10^6$ MCF-7 cells injected intraperitoneally every 3 weeks for a total of 3 to 4 injections. The mice were sacrificed three days after the last injection and their spleens were taken. A spleen cell suspension was prepared, and the resulting cell suspension was washed by two centrifugations (800×g) in protein-free Dulbecco's modified Eagles medium.

Because the antibody-producing cells obtained from the spleen do not independently reproduce, and thus cannot be cultured, they are fused with cells which may be independently cultured either in vivo or in vitro so that the genetic and metabolic processes of the fused hybridomas have characteristics of each of the parent cells, and it is intended that certain of the cells obtained will have the capability to independently reproduce and to produce the antibody of the antibody-producing parent cell. Some tumor cells, particularly myeloma cells, may be advantageously fused with antibody-producing cells to produce hybridomas. Although it is not necessary, it is preferred that the tumor cells and antibody-producing cells be derived from the same species to enhance the likelihood that the genetic and biochemical properties of the parent cells will be compatible and thus produce viable and stable hybridomas. A number of myeloma cultures have been characterized, and herein, mouse-derived, nonantibody-producing myeloma cell line, PAI that was obtained from Dr. Theo Stachlin, Basil, Switzerland, J. Stocker, *Research Disclosure* 21713, 155–157 (1982), were used to produce the hybridomas. It is to be understood that other tumor lines, which include but are not limited to P3NS1, Y3, SP2/0 and their derivatives, may also be used.

It is advantageous to select a myeloma line which does not produce antibody so that the resulting hybridoma will only produce the antibody of the parent spleen or lymph node cell. This is particularly important when the antibody is used for therapeutic purposes, e.g., as a cytotoxic agent against tumor cells, where it is undesirable to introduce extraneous antibodies which could produce side reactions.

The myeloma cells are maintained in Dulbecco's modified Eagle's medium supplemented with 10% horse serum. $10^7$ myeloma cells and $10^8$ cells obtained from the immunized mice are resuspended for fusion in a 45% solution (v/v) of polyethelyene glycol 1500. Cell hybrids are selected in hypoxanthine aminopterin thymidine (HAT) medium, all growth in HAT medium being indicative of successful hybridization of mouse spleen and mouse myeloma cells.

Clones of hybridomas may be grown in vitro according to known tissue culture techniques such as is described by Cotten et al., *Eur. J. Immunol.* 3, 136 (1973). Alternatively, hybridomas may be grown in vivo as tumors in a histocompatible animal or in athymic nude mice. The antibodies may be recovered from the in vitro culture medium (the supernatant of the clone) or from the serum or ascitic fluid of the animal by means known in the art, e.g., Gerhard et al., *Proc. Natl. Acad. Sci.*, 75, pp. 1510–1514 (1978). In some cases it may be advantageous to obtain the antibodies directly from the cells of the culture or tumor.

The initial specificity screening of hybridoma supernatants using dried MCF-7, MDA-157 and DU4475 (other mammary carcinoma cell lines which were cultured in the manner that MCF-7 was cultured) and a human foreskin fibroblast (HFF) cell line as target cells was performed by ELISA assay. Hybrids which reacted with either MCF-7 and/or MDA-157 (but not HFF cells) were chosen for a second screening.

Selected hybridomas were cultured in DMEM supplemented with 10% horse serum, NEAA, $10^{-5}$M mercaptoethanol.

When a useful hybridoma clone is produced it is generally advantageous to reclone the cell line to avoid overgrowth of cultures with variant cells no longer producing antibody. Because the hybridoma contains some, but not all, of the genetic material of each parent cell, the full characteristics of the hybridoma are not known. Often a hybridoma clone, due to original genetic deficiency or subsequent chromosome loss, after several passages may lose its ability to reproduce and/or to produce the particular antibody. Accordingly, it is important, soon after the initial hybridization, that a hybridoma clone of interest is recloned to insure that availability of functioning strains of the antibody-producing hybridoma. By recloning is meant to isolate individual hybridoma cells and expand them into cultures which are clones.

A cell line culture initially designated as 15A8 and its reclones, and other antibody-producing subcultures, produce a monoclonal antibody specific for a cell surface antigen that occurs predominantly on human mammary carcinoma cells. The 15A8 cell line is on deposit, under the terms of the Budapest Treaty and the Regulations promulgated thereunder, at the American Tissue Culture Collection of 12301 Parklawn Drive, Rockville, Md. 20852 and has been assigned the accession number HB-8655.

Antibodies of the invention will generally be of class IgM or IgG. As understood in the art, cells in an hybridoma culture, wherein the hybridomas secrete antibody that is solely or predominantly of a single subclass or isotype, may undergo class-switching, whereupon hybridoma cells occur, which secrete antibody that usually has the same idiotype (and, therefore, same antigen and epitope specificity) but has different isotype from antibody secreted by their parental cells, and antibody of more than one isotype occurs in the culture. Thus, an hybridoma culture of the invention which produces monoclonal antibody of predominantly IgM isotype might also produce monoclonal antibody of the same idiotype but of isotype IgG3, IgG2 or IgG1. Similarly, for example, a culture of predominantly IgG1 isotype antibody might also produce antibody of IgG2 class (e.g., $IgG_{2a}$ or $IgG_{2b}$ isotype).

The isotype of monoclonal antibody 15A8 was determined by Ouchterlony gel immunodiffusion with rabbit antiserum to mouse IgG1, IgG2a, IgG2b, IgG3, IgM and IgA (Miles Laboratory). 15A8 monoclonal antibody was determined to be of the IgG1 isotype. The 15A8 antibody is characterized in that it reacts with a surface antigen present in nearly all breast cancers examined, as well as with all fibrocystic diseases and normal mammary epithelium. It reacts with some other normal tissues and frequently with a number of adenocarcinomas not of breast origin. It does not react with mesotheliomas and is therefore suitable for the differential diagnosis of these cancers from metastatic breast cancer, e.g., by immunoperoxidase staining, immunofluorescence, or the like. It slows down the growth of cells of the MDA human breast cancer line in vitro.

By screening, by a procedure known in the art, and detailed below, hybridoma cells secreting antibody of isotype $IgG_{2a}$ and $IgG_{2b}$ were isolated from cultures of hybridoma 15A8, and hybridoma cultures were grown from these cells.

An hybridoma culture, designated $15A8G_{2a}$, whose cells secrete antibody of the same idiotype as antibody 15A8 and are predominantly of isotype $IgG_{2a}$, and an hybridoma culture, designated $15A8G_{2b}$, whose cells secrete antibody of the same idiotype as antibody 15A8 and are predominantly of isotype $IgG_{2b}$, have been deposited at the ATCC under the terms of the Budapest Treaty and Regulations promulgated thereunder and have been assigned deposit numbers HB-9344 (for $15A8G_{2a}$) and HB-9345 (for $15A8G_{2b}$).

The antibody from these cultures has the same reactivity with various cell types, in culture and tissue sections, as the antibody from hybridoma culture 15A8.

The 15A8 monoclonal antibody (predominantly IgG1) was purified to greater than 95% homogeneity by the following steps: ascites was obtained following injection of hybridoma cells into previously pristane-primed BALB/c mice. The resulting ascitic fluid was clarified by centrifugations at 10,000×g for 10 minutes. 45% ammonium sulfate precipitation was followed by centrifugation at 10,000×g for 10 minutes. The pellet was resuspended in 10 ml. of 20 mM Tris 0.02% NaN3 pH 8 buffer, dialyzed against the same buffer and applied to an affi-gel blue DEAE ion-exchange column. The column was washed with 3 bed volumes of 20 mM Tris plus 28 mM NaCl with 0.02% NaN3 buffer, and the antibody was eluted with a NaCl gradient. Fractions (2 ml.) were collected and an OD 280 was determined. Immunoperoxidase on human mammary tumors was used to localize fractions containing antibody. The appropriate fractions were pooled. The protein concentration was determined by the method of Lowry et al., *J. Biol. Chem.* 193, 265–275 (1975). The degree of purification was determined by polyacrylamide gel electrophoresis.

Purified 15A8 antibody (10 gm/ml) was found to be highly reactive at dilutions of 1:10,000 with MCF-7 and MDA-175 cells. By immunofluorescence, the pattern appeared to be that of surface membrane reactivity. The reactivity persisted, although reduced, following methanol-acetic acid fixation.

Portions of fresh normal and malignant tissues were obtained from the Surgical and Anatomical Pathology Departments of the UCSD Hospital and the Veterans Hospital, San Diego. Fresh frozen tissues were obtained from the biological carcinogenesis branch of the National Cancer Institute. The reactivity of the 15A8 monoclonal antibody with the several tissues was determined by immunoperoxidase staining.

Tissues were coated with Tissue Tek OCT Compound (Scientific Products) and frozen at −70° C. Sections of frozen tissue blocks 4 μM thick were cut on the microtome/cryostat, mounted on glass slides and stored at −70° C. Mounted slides were stained by an indirect immunoperoxidase assay. Briefly, slides were hydrated with PBS, then partially air-dried. The monoclonal antibody was overlayed onto sections and incubated at room temperature for 30 minutes in a humid chamber. Sections were then overlaid with a 1:100 dilution of horseradish peroxidase conjugated with goat anti-mouse immunoglobulin and incubated for 30 minutes. The color reaction was developed with diaminobenzidine (0.6 mg/ml) and 0.03% hydrogen peroxide. Cells were counterstained in hematolxylin, washed in water, dehydrated in 100% ethyl alcohol, cleared in xylene, mounted in Permount, covered with a coverslip and examined using a Zeiss microscope. The reactivities of 15A8 with human mammary carcinoma cell lines and other tumor tissues are shown in Table 1.

TABLE 1

| BINDING OF 15A8 ANTIBODY TO HUMAN MAMMARY CARCINOMA CELL LINES AND OTHER HUMAN TUMOR TISSUES | |
|---|---|
| | 15A8 |
| CELL LINES (live) | |
| Mammary carcinoma | |
| MCF-7 | + |
| MDA-157 | + |
| DU4475 | − |
| Non-mammary | |
| HFF | − |
| PA1 | − |
| TISSUES (frozen) | |
| Human mammary carcinoma (total) | +(28/31) |
| Primary infiltrating ductal carcinoma | +(16/19) |
| Infiltrating ductal cancer | +(5/5) |

TABLE 1-continued
BINDING OF 15A8 ANTIBODY TO HUMAN MAMMARY CARCINOMA CELL LINES AND OTHER HUMAN TUMOR TISSUES

| | 15A8 |
|---|---|
| metastatic to liver, lung omentum and brain | |
| Intraductal papillary, colloid mammary carcinomas | +(6/6) |
| Comedo carcinoma | +(1/1) |
| Cystosarcoma phylloides | −(1) |
| Papillary ductular hyperplasia, sclerosins adenosis | +(2/2) |
| Fibrocystic disease | +(2/2) |
| Fibroadenoma | +(2/2) |
| Normal mammary epithelium | +(4/4) |

+ = positive immunoperoxidase reaction (usually strong)
− = no reaction
* = weak reaction Table 2 below summarizes the reactivities of 15A8 with normal tissues and nonmammary malignancies. 15A8 had crossreactivities with normal breast, renal proximal tubule, epidermal, esophageal, and salivary gland epithelium, and with one specimen each of cervical, colon and prostate carcinomas. 15A8 stained 3 of 6 specimens of known estrogen receptor and progresterone receptor negative breast carcinomas, but stained all four specimens of known estrogen receptor and/or progesterone receptor positive breast carcinomas.

TABLE 2
BINDING OF ANTIBODY 15A8 TO NORMAL TISSUES AND NONMAMMARY MALIGNANCIES

| | 15A8 |
|---|---|
| NORMAL TISSUES | |
| Epidermis | + |
| Salivary gland | + |
| Thyroid | − |
| Adrenal | − |
| Lung | − |
| Bronchus | − |
| Heart | − |
| Aorta | − |
| Esophagus | + |
| Stomach | − |
| Small bowel | − |
| Large bowel | − |
| Liver (2) | − |
| Pancreas | − |
| Gall bladder | − |
| Spleen | − |
| Lymph nodes | − |
| Kidney (2) | prox tubule + |
| Bladder | − |
| Ovary | − |
| Testis | − |
| Cervix | − |
| Uterus | − |
| Bone marrow | − |
| Brain | − |
| NONMAMMARY MALIGNANCIES | |
| *Lung* | |
| Squamous cell cancer | + |
| Adenocarcinoma | − |
| Small cell cancer | − |
| *Gastrointestinal* | |
| Gastric cancer | − |
| Cholangiocarcinoma | − |
| Pancreatic cancer | − |
| Colon cancer (2) | −/+ |
| *Genito-urinary* | |
| Cervix cancer | + |
| Ovarian cancer | − |
| Bladder cancer | − |
| Renal cancer | − |
| Prostate cancer (2) | −/+ |
| Lymphoma | − |
| T cell | − |
| Mesothelioma | − |
| Melanoma | − |

Because 15A8 antibody detects antigens found predominantly in human mammary carcinomas, this antibody is presently useful for diagnosing mammary carcinoma cells and should prove useful in future studies of the lineage patterns of these tumor cells. 15A8 may also have application in both tumor localization and therapy because it is exposed at the cell surface. There is evidence that the antibody, in an immunotoxin formed by conjugating the antibody, using SPDP, to an average of 1-2 gelonin molecules per antibody molecule, might be effective therapeutically against breast cancer.

Hybridoma cultures producing antibody of the same idiotype as the antibody from culture 15A8, but predominantly of isotype $IgG_{2a}$ or $IgG_{2b}$ rather than IgG1, were prepared from culture 15A8 as follows:

Logarithmically growing cells of 15A8-G1 parent were plated at a density of 1000 cells per well in 96-well microtiter dishes in DMEM containing 10% horse serum, $10^{-5}$M 2-mercaptoethanol and 1% non-essential amino acids (HMAA). The cultures were incubated for 7-10 days in 12% $CO_2$ at 37° C. A total of 960 wells were screened for the presence of cells producing $G_{2a}$ or $G_{2b}$ variants using a sensitive isotype-specific micro-Elisa assay. The assay for isotype variants employed an isotype-specific capture antibody coated in wells of 96-well dishes and a horseradish peroxidase-linked isotype-specific detecting antibody. Immulon 2 (Dynatech) plates were coated with 100 ul/well rabbit anti-mouse $IgG_{2a}$ (Zymed) diluted 1:1000 in 10 mM borate, 150 mM NaCl, pH 8.5 (borate-buffered saline) by incubating overnight at 4° C. Unreacted binding sites in the plates were blocked by a one-hour incubation with 200 ul/well 1% bovine serum albumin in borate-buffered saline at room temperature. 100 ul of culture supernatant from each well of the parental culture were added to the capture antibody plates, and the plates incubated for 4 hours at 37° C. in 12% $CO_2$. The culture supernatants were removed after the 4 hour incubation and the wells washed 4 times with borate-buffered saline. 100 ul/well of horseradish peroxidase linked goat anti-mouse $IgG_{2a}$ (Southern Biotechnology Associates) diluted 1:1000 in 1% bovine serum albumin in borate-buffered saline was added overnight at 4° C. The detecting antibody was removed, the plates washed 4 times in borate-buffered saline, and 150 ul/well of substrate added (O-phenylenediamine, 0.4 mg/ml and 75 mM citrate pH 5.5, and 0.015% hydrogen peroxide) for 30 minutes. The reaction was stopped with 50 ul/well of 4N $H_2SO_4$ and read at 490 nm using a microplate reader.

$IgG_{2b}$ variants were detected in the same way using rabbit anti-mouse $IgG_{2b}$ capture antibody and HRP-goat anti-mouse $IgG_{2b}$ detecting antibody.

Positive wells showing secretion of variant isotypes were replated in 96-well dishes at 20 cells/well and the selection repeated. Positive wells from this selection were then cloned by limiting dilution at one cell per five wells and screened again by micro-Elisa. The variants, after cloning, were checked for reaction to MCF-7 cells and breast tumor sections and found to react positively.

The best producing of the hybridoma cultures producing predominantly $IgG_{2a}$ or $IgG_{2b}$ antibody with the specificity of 15A8 produce, in both culture supernatants and ascites fluid from mice inoculated intraperitoneally with hybridoma cells, significantly more antibody than the best producing of the cultures producing IgG1 15A8 antibody, the $G_{2a}$-producing variants (e.g. the cultures on deposit of ATCC under deposit number HB9344) producing 4–5 fold more antibody than the G1-producing parent and the $G_{2b}$-producing variant (e.g. the culture on deposit at the ATCC under deposit number HB-9345) producing 2–3 fold more antibody than the G1-producing parent.

The three isotypes of 15A8 (IgG1, $IgG_{2a}$, $IgG_{2b}$) have been tested and compared for the following properties:

1. Staining of "normal" human tissues by immunoperoxidase is the same for all three isotypes. That is, the three isotypes positively stain epithelia of the breast, skin, esophagus, salivary, kidney tubule, and bladder, and show no positive staining for other tissues.
2. Staining of primary site carcinomas of the breast, bladder, kidney, and esophagus. All isotypes show identical staining patterns.

Purified 15A8 antibody of all three isotypes has been tested for potential use in serotherapy on human breast tumors growing in nude mice. The results with all three isotypes to date have been negative, although the $IgG_{2a}$ isotype antibody might still prove to be useful in serotherapy of breast cancer.

The antigen recognized by the 15A8 antibodies has been isolated from MCF-7 cells employing the IgG1 isotype antibody. The antigen is a 22,000 dalton plasma membrane protein. The epitope on this protein that is recognized by the monoclonal antibodies is no longer recognized by them after treatment of the antigen with aldehyde fixatives (e.g. treatment with 3%–10% formaldehyde or 0.1%–2% glutaraldehyde in neutral-buffered saline) or denaturation of the antigen by heat (100° C. for ten minutes).

Of particular significance is the fact that the monoclonal antibody does not react with mesothelioma cells. Although these cells are not mammary tumor cells, they often occur at the same site as metastatic mammary carcinomas, and the 15A8 antibody is therefore particularly useful for distinguishing metastasized carcinomas from mesothelioma tumors.

Modifications obvious to one with ordinary skill in the art may be made without departing from the scope of the present invention. For example, antibody production may be induced in the host animal by inoculating the animal with cell membrane fragments or cell membrane derived material rather than with complete mammary tumor cells.

Various features of the invention are set forth in the following claims.

What is claimed is:

1. A culture of an hybridoma which is a culture with the characteristics of the culture of hybridoma 15A8, on deposit at the ATCC under deposit number HB-8655, or an antibody-producing subculture of such culture, wherein said hybridoma secretes an IgG1 or IgG2 antibody which binds to an epitope on an antigen which occurs in the plasma membrane of MCF-7 cells, said epitope being exposed on the extracellular side of said membrane on said cells in culture, and said antigen having a molecular weight of approximately 22 kD; wherein the binding of the secreted antibody to said epitope is substantially eliminated by treatment of said antigen with an aldehyde fixative or denaturation of said antigen with heat.

2. A culture of hybridoma which is a culture with the characteristics of the culture of hybridoma $15A8G_{2a}$, on deposit at the ATCC under deposit number HB-9344, or an antibody-producing subculture of such culture, wherein said hybridoma secretes an IgG1 or IgG2 antibody which binds to an epitope on an antigen which occurs in the plasma membrane of MCF-7 cells, said epitope being exposed on the extracellular side of said membrane on said cells in culture, and said antigen having a molecular weight of approximately 22 kD; wherein the binding of the secreted antibody to said epitope is substantially eliminated by treatment of said antigen with an aldehyde fixative or denaturation of said antigen with heat.

3. A culture of hybridoma which is a culture with the characteristics of the culture of hybridoma $15A8G_{2b}$, on deposit at the ATCC under deposit number HB-9345, or an antibody-producing subculture of such culture; wherein said hybridoma secretes an IgG1 or IgG2 antibody which binds to an epitope on an antigen which occurs in the plasma membrane of MCF-7 cells, said epitope being exposed on the extracellular side of said membrane on said cells in culture, and said antigen having a molecular weight of approximately 22 kD; wherein the binding of the secreted antibody to said epitope is substantially eliminated by treatment of said antigen with an aldehyde fixative or denaturation of said antigen with heat.

4. A monoclonal IgG1 or IgG2 antibody produced by a culture with the characteristics of the culture of hybridoma 15A8, on deposit at the ATCC under deposit number HB-8655, or an antibody-producing subculture of such culture, wherein said antibody binds to an epitope on an antigen which occurs in the plasma membrane of MCF-7 cells, said epitope being exposed on the extracellular side of said membrane on said cells in culture, and said antigen having a molecular weight of approximately 22 kD, wherein the binding of the secreted antibody to said epitope is substantially eliminated by treatment of said antigen with an aldehyde fixative or denaturation of said antigen with heat.

5. A monoclonal IgG1 or IgG2 antibody produced by a culture with the characteristics of the culture of hybridoma $15A8G_{2a}$, on deposit at the ATCC under deposit number HB-9344, or an antibody-producing subculture of such culture, wherein said antibody binds to an epitope on an antigen which occurs in the plasma membrane of MCF-7 cells, said epitope being exposed on the extracellular side of said membrane on said cells in culture, and said antigen having a molecular weight of approximately 22 kD, wherein the binding of the secreted antibody to said epitope is substantially eliminated by treatment of said antigen with an aldehyde fixative or denaturation of said antigen with heat.

6. A monoclonal IgG1 or IgG2 antibody produced by a culture with the characteristics of the culture of hybridoma $15A8G_{2b}$, on deposit at the ATCC under deposit number HB-9345, or an antibody-producing subculture of such culture, wherein said antibody binds to an epitope on an antigen which occurs in the plasma membrane of MCF-7 cells, said epitope being exposed on the extracellular side of said membrane on said cells in culture, and said antigen having a molecular weight of approximately 22 kD, wherein the binding of the secreted antibody to said epitope is substantially eliminated by treatment of said antigen with an aldehyde fixative or denaturation of said antigen with heat.

7. An antibody according to claim 4 which is of isotype IgG1.

8. An antibody according to claim 5 which is of isotype $IgG_{2a}$.

9. An antibody according to claim 6 which is of isotype $IgG_{2b}$.

* * * * *

UNITED STATES PATENT AND TRADEMARK OFFICE
CERTIFICATE OF CORRECTION

PATENT NO. : 5,032,521

DATED : 8/8/91

INVENTOR(S) : White, et al.

It is certified that error appears in the above-identified patent and that said Letters Patent is hereby corrected as shown below:

On the title page, Item: [56], 2nd Ref., under the "Allen et al.," reference, change "1203-1027" to --1203-1207--; 3rd Ref., under the "Ciocca" reference, change "Immunchistochemical" to --Immunohistochemical--; 4th Ref., under "Colcher et al,", change "Moncolonal" to --Monoclonal--; 5th Ref., under the "Taylor-Papadimitriou" reference, change "Monocclonal" to --Monoclonal--; 7th Ref., under the "Stocker et al," reference, change "PAI" to --'PAI'--, and "PAI-O" to --'PAI-O'--. IN FOREIGN REFERENCES: [56], Line 3, under the third European patent Off., change the number from "02424154" to --0242154--.
: Column 1, line 40, delete second occurrence "were"; line 51, change "an hybridoma" to --a hybridoma--; line 56, change "an hybridoma" to --a hybridoma--; line 60, change "an hybridoma" to --a hybridoma--. Column 2, line 11, change "an hybridoma" to --a hybridoma--; line 50, only one paragraph of the insert was inserted into the patent. Lines 9-40 were left out, should be inserted; (See attached sheets).

UNITED STATES PATENT AND TRADEMARK OFFICE
CERTIFICATE OF CORRECTION

PATENT NO. : 5,032,521
DATED : July 16, 1991
INVENTOR(S) : Christine A. White, et. al.

It is certified that error appears in the above-indentified patent and that said Letters Patent is hereby corrected as shown below:

Antibody from hybridoma culture 15A8 is predominantly of IgG1 isotype. By a standard screening technique, hybridomas were isolated from cultures of 15A8 which produce antibody of $IgG_{2a}$ or $IgG_{2b}$ isotype. Representative cultures of these hybridomas are designated $15A8G_{2a}$ (which produces antibody which is solely or predominantly of $IgG_{2a}$ isotype) and $15A8G_{2b}$ (which produces antibody which is solely or predominantly of $IgG_{2b}$ isotype). The idiotype of the class IgG2 antibodies, which are produced in cultures of 15A8, $15A8G_{2a}$ and $15A8G_{2b}$, is the same as that of the class IgG1 antibody produced in cultures of 15A8. Thus, the antibodies of the invention, of $IgG_{2a}$ and $IgG_{2b}$ isotypes, are useful diagnostically and, potentially, therapeutically in the same way as the antibody of IgG1 isotype. It is thought that the antibody of isotype $IgG_{2a}$ might also be useful by itself, not conjugated to a toxin, in treating mammary tumors.

UNITED STATES PATENT AND TRADEMARK OFFICE
CERTIFICATE OF CORRECTION

PATENT NO. : 5,032,521
DATED : July 16, 1991
INVENTOR(S) : Christine A. White, et. al.

It is certified that error appears in the above-indentified patent and that said Letters Patent is hereby corrected as shown below:

The antigen in MCF-7 cells recognized by the antibodies of the invention is a 22 kD protein that occurs in the plasma membrane of the cells in culture. The epitope of this antigen which is recognized by the 15A8 antibodies of the invention (of IgG1, $IgG_{2a}$ and $IgG_{2b}$ isotypes) is disrupted, and made unrecognizable by the antibodies, by treatment of the antigen with an aldehyde fixative (e.g., formaldehyde or glutaraldehyde) or denaturation of the antigen by heat.

Column 3,
line 31, after "human mammary' insert --carcinoma tissues--.
Column 4, line 66, delete "that" after "insure".  Column 5, line 11, between "20852" and "and" insert --("ATCC")--; line 14,

UNITED STATES PATENT AND TRADEMARK OFFICE
CERTIFICATE OF CORRECTION

PATENT NO. : 5,032,521
DATED : 8/8/91
INVENTOR(S) : White, et al.

It is certified that error appears in the above-identified patent and that said Letters Patent is hereby corrected as shown below:

change "an hybridoma" to --a hybridoma--; line 23, change "an hybridoma" to --a hybridoma--; line 51, change "An hybridoma" to --A hybridoma--; line 53, change "an hybridoma" to --a hybridoma--; line 66, change "was" to --were--. Column 6, line 18, change "(10 gm/ml)" to --(10 mg/ml)--. Column 7, line 26, change "progresterone" to --progesterone--. Column 8, line 34, change "micro-Elisa" to --micro-ELISA--; line 68, change "micro-Elisa" to --micro-ELISA--. Column 9, line 16, change "IgG2*a*" to --IgG$_{2a}$--; line 60, change "an hybridoma" to --a hybridoma--.

Signed and Sealed this

Twenty-ninth Day of June, 1993

MICHAEL K. KIRK

Acting Commissioner of Patents and Trademarks